United States Patent
Jiao et al.

(10) Patent No.: US 11,725,252 B2
(45) Date of Patent: Aug. 15, 2023

(54) **PCR DETECTION KIT FOR RAPIDLY IDENTIFYING *SALMONELLA* OF SPECIFIC SEROTYPES**

(71) Applicant: YANGZHOU UNIVERSITY, Yangzhou (CN)

(72) Inventors: Xinan Jiao, Yangzhou (CN); Zhiming Pan, Yangzhou (CN); Dan Xiong, Yangzhou (CN); Li Song, Yangzhou (CN); Yang Jiao, Yangzhou (CN); Lin Sun, Yangzhou (CN); Xiang Chen, Yangzhou (CN); Shizhong Geng, Yangzhou (CN); Jinlin Huang, Yangzhou (CN); Yuelan Yin, Yangzhou (CN)

(73) Assignee: YANGZHOU UNIVERSITY, Yangzhou (CN)

( * ) Notice: Subject to any disclaimer, the term of this patent is extended or adjusted under 35 U.S.C. 154(b) by 983 days.

(21) Appl. No.: 16/311,709

(22) PCT Filed: Nov. 18, 2016

(86) PCT No.: PCT/CN2016/106398
§ 371 (c)(1),
(2) Date: Oct. 4, 2019

(87) PCT Pub. No.: WO2017/219597
PCT Pub. Date: Dec. 28, 2017

(65) Prior Publication Data
US 2020/0024647 A1    Jan. 23, 2020

(30) Foreign Application Priority Data
Jun. 22, 2016   (CN) .......................... 201610459944.4

(51) Int. Cl.
C12Q 1/689   (2018.01)
C12Q 1/10    (2006.01)

(52) U.S. Cl.
CPC ............... *C12Q 1/689* (2013.01); *C12Q 1/10* (2013.01)

(58) Field of Classification Search
None
See application file for complete search history.

(56) References Cited

U.S. PATENT DOCUMENTS

2006/0068433 A1 * 3/2006 Godfrey ................. C12Q 1/686
                                                            435/6.18
2009/0203032 A1 * 8/2009 Shanks .................. C12Q 1/689
                                                            435/6.15

OTHER PUBLICATIONS

Newman, Identification and Characterization of a Novel Bacterial Virulence Factor That Shares Homology with Mammalian Toll/Interleukin-1 Receptor Family Proteins, Infection and Immunity, 74(1): 594-601, 2006. (Year: 2006).*
Gen Bank Accession No. KM408432.1, 2019. (Year: 2019).*
Gen Bank Accession No. KM408432.1, revision history. (Year: 2015).*

* cited by examiner

*Primary Examiner* — Angela M. Bertagna
*Assistant Examiner* — Carolyn L Greene
(74) *Attorney, Agent, or Firm* — Tianhua Gu; Global IP Services

(57) ABSTRACT

The present disclosure relates to a PCR detection kit for rapidly identifying *Salmonella* of specific serotypes. The kit includes primers for detecting tcpS gene, the primers for detecting the tcpS gene including a forward primer having a nucleotide sequence as set forth in SEQ ID NO. 1 and a reverse primer having a nucleotide sequence as set forth in SEQ ID NO. 2. The kit can identify *Salmonella* of *enteritidis, pullorum/gallinarum*, and *dublin* serotypes rapidly and in a high throughput, which can be used as an auxiliary method for the conventional serotyping of *Salmonella*.

3 Claims, 12 Drawing Sheets

Specification includes a Sequence Listing.

FIG. 1

| Description | Max score | Total score |
|---|---|---|
| Salmonella enterica subsp. enterica serovar Enteritidis strain FORC_007, complete genome | 1629 | 1629 |
| Salmonella enterica subsp. enterica serovar Enteritidis strain C50041 TcpS (tcpS) gene, complete cds | 1629 | 1629 |
| Salmonella enterica subsp. enterica serovar Pullorum str. ATCC 9120, complete genome | 1629 | 1629 |
| Salmonella enterica subsp. enterica serovar Enteritidis strain SEE2, complete genome | 1629 | 1629 |
| Salmonella enterica subsp. enterica serovar Enteritidis strain SEE1, complete genome | 1629 | 1629 |
| Salmonella enterica subsp. enterica serovar Enteritidis str. EC20120005, complete genome | 1629 | 1629 |
| Salmonella enterica subsp. enterica serovar Enteritidis str. EC20120002 genome | 1629 | 1629 |
| Salmonella enterica subsp. enterica serovar Enteritidis str. EC20090641, complete genome | 1629 | 1629 |
| Salmonella enterica subsp. enterica serovar Enteritidis str. 18569, complete genome | 1629 | 1629 |
| Salmonella enterica subsp. enterica serovar Enteritidis strain OLF-SE2-98984-6, complete genome | 1629 | 1629 |
| Salmonella enterica subsp. enterica serovar Enteritidis strain OLF-SE3-98983-4, complete genome | 1629 | 1629 |

FIG. 1A

| Query cover | E value | Ident | Accession |
|---|---|---|---|
| 100% | 0.0 | 100% | CP009768.1 |
| 100% | 0.0 | 100% | KM408432.1 |
| 100% | 0.0 | 100% | CP012347.1 |
| 100% | 0.0 | 100% | CP011791.1 |
| 100% | 0.0 | 100% | CP011790.1 |
| 100% | 0.0 | 100% | CP007267.2 |
| 100% | 0.0 | 100% | CP007329.2 |
| 100% | 0.0 | 100% | CP007249.2 |
| 100% | 0.0 | 100% | CP011394.1 |
| 100% | 0.0 | 100% | CP009084.2 |
| 100% | 0.0 | 100% | CP009085.2 |

FIG. 1B

| | | |
|---|---|---|
| Salmonella enterica subsp. enterica serovar Gallinarum str. 287/91 complete genome | 1629 | 1629 |
| Salmonella enterica subsp. enterica serovar Enteritidis strain OLF-SE1-1019-1, complete genome | 1629 | 1629 |
| Salmonella enterica subsp. enterica serovar Enteritidis strain OLF-SE5-1104-2, complete genome | 1629 | 1629 |
| Salmonella enterica subsp. enterica serovar Enteritidis strain OLF-SE4-0317-8, complete genome | 1629 | 1629 |
| Salmonella enterica subsp. enterica serovar Enteritidis strain OLF-SE11-10058, complete genome | 1629 | 1629 |
| Salmonella enterica subsp. enterica serovar Enteritidis strain OLF-SE10-10052, complete genome | 1629 | 1629 |
| Salmonella enterica subsp. enterica serovar Enteritidis strain OLF-SE9-10012, complete genome | 1629 | 1629 |
| Salmonella enterica subsp. enterica serovar Enteritidis strain OLF-SE7-100819, complete genome | 1629 | 1629 |
| Salmonella enterica subsp. enterica serovar Dublin genome assembly SC50_1, chromosome : I | 1629 | 1629 |
| Salmonella enterica subsp. enterica serovar Pullorum genome assembly S44987_1, chromosome : I | 1629 | 1629 |
| Salmonella enterica subsp. enterica serovar Enteritidis str. 77-1427, complete genome | 1629 | 1629 |

FIG. 1C

| | | | |
|---|---|---|---|
| 100% | 0.0 | 100% | AM933173.1 |
| 100% | 0.0 | 100% | CP009083.1 |
| 100% | 0.0 | 100% | CP009087.1 |
| 100% | 0.0 | 100% | CP009086.1 |
| 100% | 0.0 | 100% | CP009093.1 |
| 100% | 0.0 | 100% | CP009092.1 |
| 100% | 0.0 | 100% | CP009091.1 |
| 100% | 0.0 | 100% | CP009089.1 |
| 100% | 0.0 | 100% | LK931502.1 |
| 100% | 0.0 | 100% | LK931482.1 |
| 100% | 0.0 | 100% | CP007598.1 |

FIG. 1D

PCR DETECTION KIT FOR RAPIDLY IDENTIFYING SALMONELLA OF SPECIFIC SEROTYPES

CROSS REFERENCE TO RELATED PATENT APPLICATION

The present application is the US national stage of PCT/CN2016/106398 filed on Nov. 18, 2016, which claims the priority of the Chinese patent application No. 201610459944.4, filed on Jun. 22, 2016, which application is incorporated herein by reference.

BACKGROUND OF THE PRESENT INVENTION

Field of Invention

The present application belongs to the field of biotechnology detection, and particularly relates to a PCR (Polymerase Chain Reaction) detection kit for rapidly identifying *Salmonella* of specific serotypes.

Description of Related Arts

Salmonellosis is one of zoonotic diseases of public health significance. Its pathogen *Salmonella* belongs to enterobacteriaceae. Eggs, livestock and meat products are main transmission media. *Salmonella* not only can cause various livestock and poultry diseases, systemic sepsis and enteritis, but also can act as the pathogen of food-borne diseases, causing human gastroenteritis and food poisoning. In China, about 70%-80% of bacterial food poisoning is caused by *Salmonella*. At present, there are more than 2500 serotypes of *Salmonella* according to the Kauffman-White (K-W) serotyping method and based on the difference of *Salmonella* somatic antigen and flagella antigen. 292 different serotypes have been reported in China, which belongs to 35 O serogroups.

Traditional detection methods, such as non-selective and selective enrichment of bacteria, biochemical characteristics and serological identification, are laborious and time-consuming, which takes 4-7 days to complete detection. Other methods such as antibody detection are fast, but their high false positives make them unsuitable for routine detection. In addition, the low level of pathogen contamination, the "injury" of *Salmonella* caused by food processing and the interference of other food ingredients have limited the detection of *Salmonella*. Therefore, in order to detect pathogenic bacteria in time, control pollution and harm to human health, rapid, specific and sensitive detection methods are urgently needed.

SUMMARY OF THE PRESENT INVENTION

The present application aims to provide a PCR detection kit for rapidly identifying *Salmonella* of specific serotypes and preparation and application thereof.

The present application provides a PCR detection kit for rapidly identifying *Salmonella* of specific serotypes. The kit comprises primers for detecting the tcpS gene. The primers for detecting the tcpS gene comprise a forward primer having a nucleotide sequence as set forth in SEQ ID NO. 1 and a reverse primer having a nucleotide sequence as set forth in SEQ ID NO. 2.

The kit according to the present application conducts tcpS gene detection with a PCR detection technology, and can analyze and judge whether a detection object belongs to one of *Salmonella enteritidis*, *Salmonella pullorum/gallinarum* or *Salmonella dublin* according to amplification and detection. Therefore, the design of primers is the key point of the kit according to the present application.

The kit according to the present application conducts detection with the PCR technology, so the kit may also comprise other conventional reagents required for PCR, such as one or more of sterile water ($ddH_2O$), dNTP, PCR buffer, rTaq enzyme, and a sample genomic DNA extraction reagent, etc. Since these common PCR reagents can be purchased separately from the market or prepared by oneself, reagents needing to be put into the kit can be provided according to actual needs of customers, or all the reagents can be put into the kit for convenience.

The kit according to the present application may contain a primer pair individually packaged or contain a prepared PCR detection solution containing a primer pair.

The PCR detection solution can be prepared by oneself or can be obtained by directly adding primers to a commercially available universal PCR detection solution without primers. For example, the kit may also contain sterile water ($ddH_2O$), dNTP, PCR buffer and rTaq enzyme. A PCR reaction system can be obtained by adding the primers according to the present application, a DNA extract of a sample to be detected or a sample bacteria solution.

Preferably, the kit may further contain a positive control. The positive control is a DNA sample containing tcpS gene expression.

Preferably, the kit may further contain a negative control. The negative control may be a DNA sample without tcpS gene expression.

The present application further provides a using method of the aforementioned PCR detection kit for rapidly identifying *Salmonella* of specific serotypes, comprising the following steps: (1) extracting sample genomic DNA; (2) adding samples: adding the sample genomic DNA, a positive control or a negative control into PCR tubes of PCR reaction systems respectively to obtain a corresponding sample reaction tube, positive reaction tube or negative reaction tube, wherein the PCR reaction systems contain the aforementioned primers for detecting the tcpS gene; (3) performing PCR reaction: placing the reaction tubes on a PCR instrument, setting circulation parameters, and performing PCR reaction; and (4) analyzing results after the PCR reaction is completed.

Preferably, the method is a method not for a disease diagnosis purpose.

In step (1), extracting sample genomic DNA is the prior art.

Preferably, in step (3), PCR reaction conditions are set to be: (a) maintaining at 94° C. for 5 min; (b) maintaining at 94° C. for 45 s; (c) maintaining at 59° C. for 45 s; (d) maintaining at 72° C. for 1 min, performing (b) to (d) for 30 times, cycles for steps (b) to (d), and then (e) maintaining at 72° C. for 10 min.

The present application also provides application of the aforementioned kit in preparation of a tcpS gene detection product.

Preferably, the detection product is used for detecting and screening one of *Salmonella enteritidis*, *Salmonella pullorum/gallinarum* and *Salmonella dublin*.

Compared with the prior art, the present application has the following beneficial effects:

through research, it is found for the first time that the tcpS gene only exists in *Salmonella* of *enteritidis*, *pullorum/gallinarum*, and *dublin* serotypes, and the distribution of the tcpS gene in different *Salmonella* serotypes and other bacteria is verified by the PCR technology with specific primers. The kit according to the present application can identify *Salmonella* of *enteritidis, pullorum/gallinarum*, and Dublin serotypes rapidly and in a high throughput, which can be used as an auxiliary method for the conventional serotyping of *Salmonella*, and provides a simple and rapid method with good repeatability for monitoring and laboratory diagnosis of *Salmonella* of the three specific serotypes.

BRIEF DESCRIPTION OF THE DRAWINGS

Figure 1:
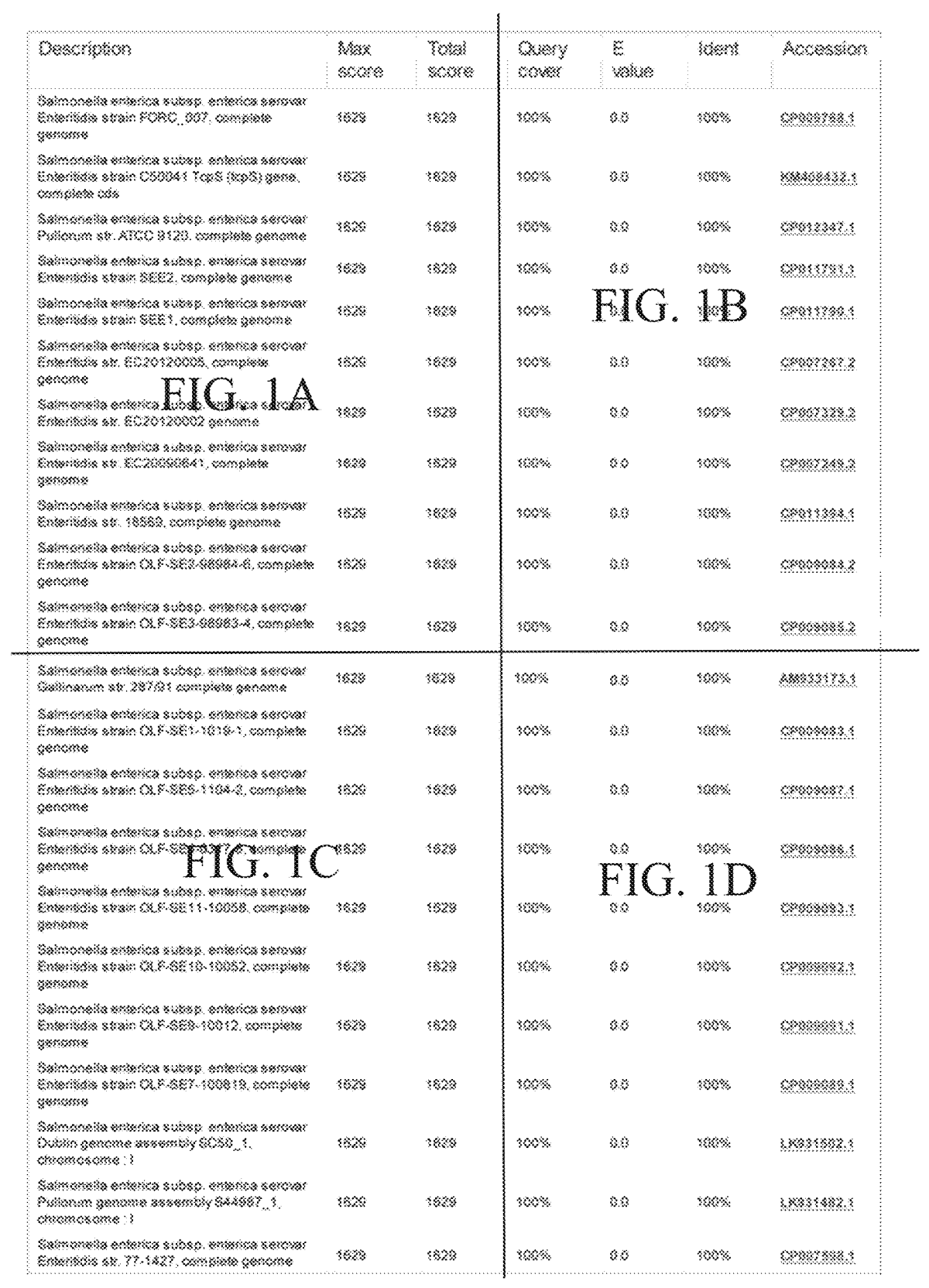

FIGS. 1A, 1B, 1C, and 1D are the parts of 1A, 1B, 1C, and 1D shown in the FIG. 1.

DETAILED DESCRIPTION OF THE PREFERRED EMBODIMENTS

Figure 2:
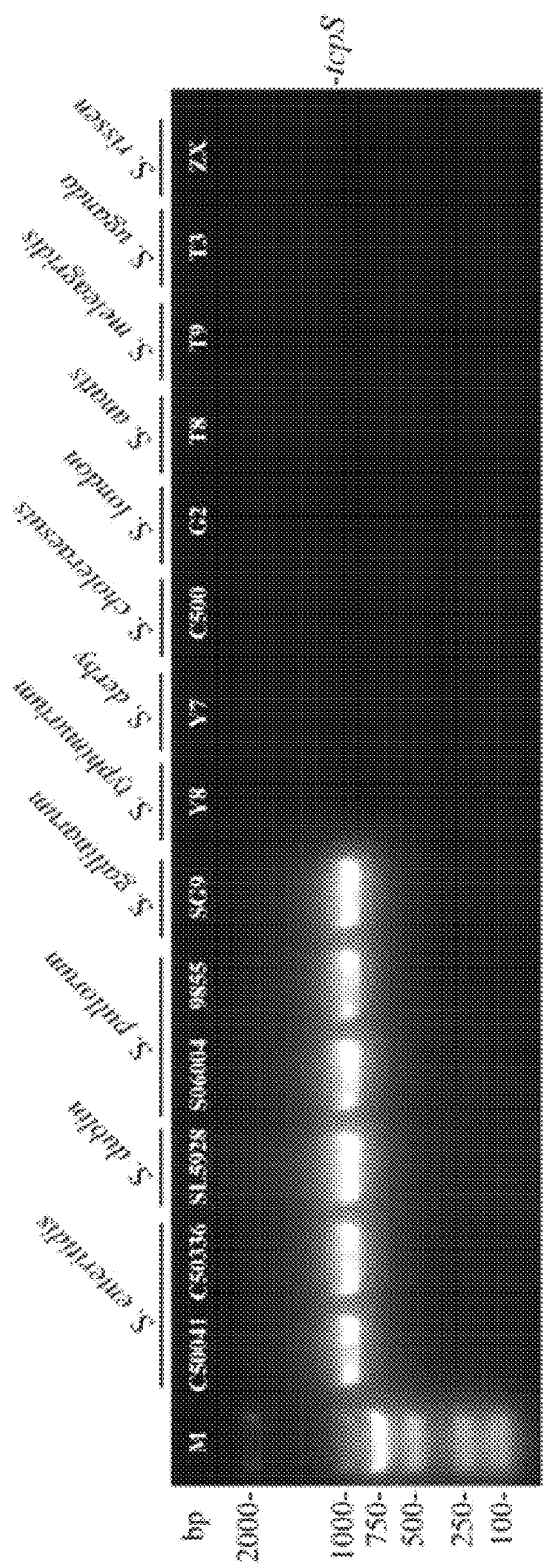
FIG. 2 is a picture of the tcpS gene distributed in *Salmonella* of different serotypes identified by PCR, wherein a lane M is DL2000 Marker; lanes C50041, C50336, SL5928, S06004, 9855 and SG9 are tcpS gene (882 bp with target band); C50041 and C50336 are *Salmonella enteritidis*, SL5928 is *Salmonella dublin*, S06004 and 9855 are *Salmonella pullorum*, SG9 is *Salmonella gallinarum*, Y8 is *Salmonella typhimurium*, Y7 is *Salmonella derby*, C500 is *Salmonella choleraesuis*, G2 is *Salmonella london*, T8 is *Salmonella anatis*, T9 is *Salmonella meleagridis*, T3 is *Salmonella uganda*, and ZX is *Salmonella rissen*.

Before further describing the specific embodiments of the present disclosure, it should be understood that the scope of protection of the present disclosure is not limited to the specific embodiments described below; and it should also be understood that the terminology used in the embodiments of the present disclosure is for the purpose of describing particular specific embodiments and is not intended to limit the scope of protection of the present disclosure.

When the embodiments give numerical ranges, it should be understood that unless otherwise stated in the present disclosure, both endpoints of each numerical range and any numerical value between the two endpoints can be selected. Unless otherwise defined, all technical and scientific terms used in the present disclosure have the same meaning as commonly understood by those skilled in the art. In addition to specific methods, equipment, and materials used in the embodiments, any method, equipment, and materials of the prior art similar to or equivalent to the methods, equipment, and materials described in the embodiments of the present disclosure may be used to implement the present disclosure according to the knowledge of the prior art by those skilled in the art and the description of the present disclosure.

Embodiment 1 Bioinformatics Method to Identify Distribution of tcpS Gene

This application incorporates by reference a Sequence Listing with this application as an ASCII text file entitled "SEQ.TXT" created on Oct. 4, 2019 and having a size of 1 KB.

Embodiment 2 Preparation of Kit

Primer design and synthesis: by using the tcpS gene as a template, primers were designed and analyzed, an optimal primer pair for detection was selected therefrom according to the genomic DNA sequence, and its nucleotide sequence is shown in Table 1:

TABLE 1

| Detection object | Primers | 5'-3' | Number |
|---|---|---|---|
| tcpS gene | Forward primer tcpS-F | ATGTCTATAAGCACCACAATG | SEQ ID NO. 1 |
|  | Reverse primer tcpS-R | TCATTTCAATAATGATTCAAGC | SEQ ID NO. 2 |

The primer pair can be individually packaged or prepared into a PCR detection solution. In the PCR detection solution, the amount of the primer pair can be the conventional amount known to those skilled in the art.

That is, the kit according to the present disclosure may contain a primer pair individually packaged, or a prepared PCR detection solution containing a primer pair.

Further, the kit may also contain sterile water (ddH$_2$O), dNTP, PCR buffer, rTaq enzyme, a sample genomic DNA extraction reagent, etc.

Embodiment 3 Kit Identified that tcpS Gene Existed Only in *Salmonella* of Specific Serotypes By using the primers in the kit according to Embodiment 2 and taking genomes of *Salmonella* of different serotypes and other bacteria as templates, the distributions of the tcpS gene in different bacteria were identified with a PCR method.

A PCR reaction system was (25 μL): ddH$_2$O 16.25 μL, dNTP 2 μL, 10× PCR buffer 2.5 μL, tcpS-F 1 μL, tcpS-R 1 μL, template 2 μL, rTaq enzyme 0.25 μL.

The PCR procedure was maintaining at 94° C. for 5 min; maintaining at 94° C. for 45 s, at 59° C. for 45 s, at 72° C. for 1 min as a cycle, performing this cycle for 30 times; and then maintaining at 72° C. for 10 min.

Figure 3:
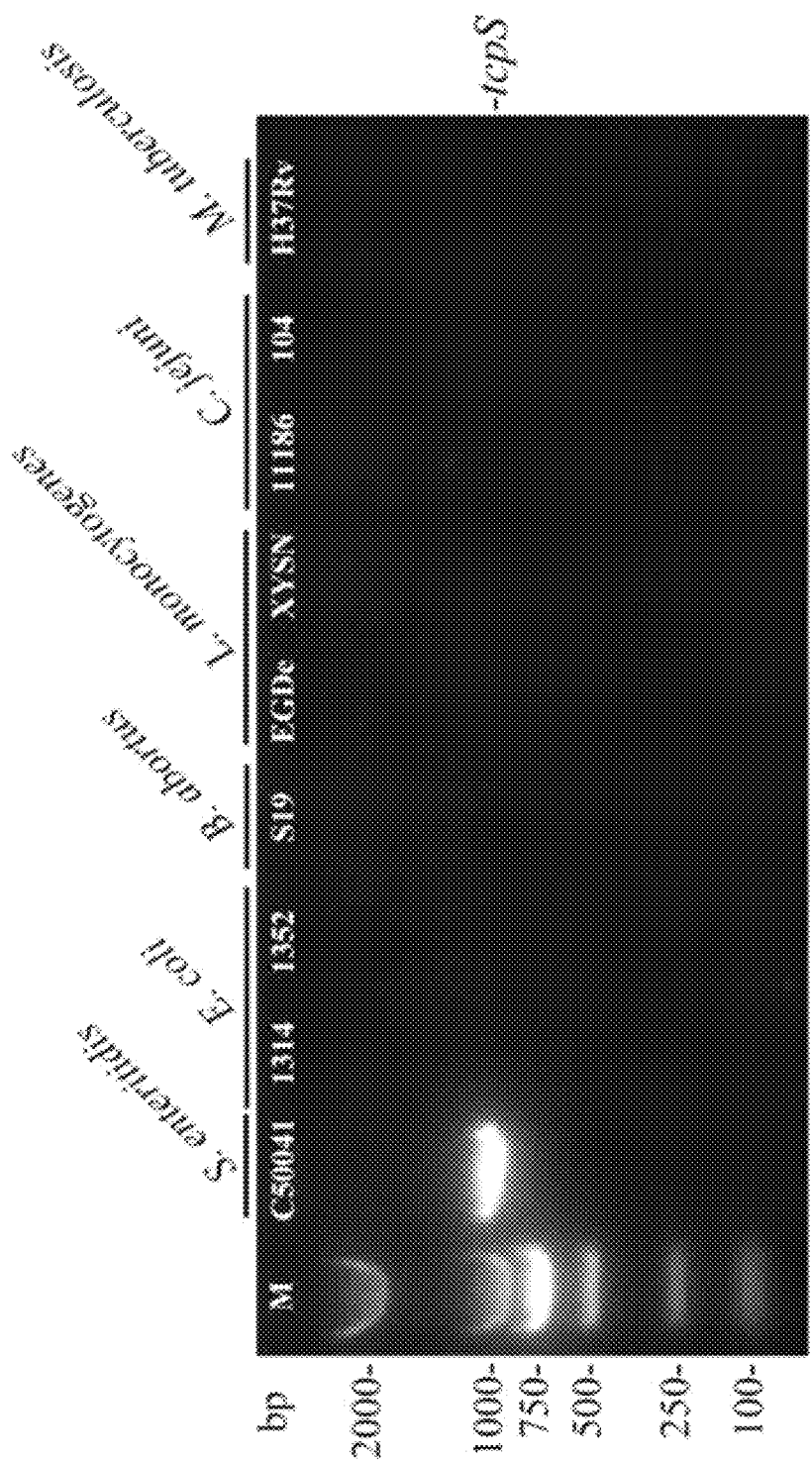
FIG. 3 is a picture of the tcpS gene distributed in different bacteria identified by PCR, wherein the lane M is DL2000 Marker; the lane C50041 is tcpS gene (882 bp with target band); C50041 is *Salmonella enteritidis*, 1314 and 1352 are *Escherichia coli*, S19 is *Brucella*, EGDe and XYSN are *Listeria*, 11186 and 104 are *Campylobacter jejuni*, and H37Rv is *Mycobacterium tuberculosis*.

PCR products were subjected to 1% agarose gel electrophoresis. PCR electrophoresis results showed that only lanes using *Salmonella enteritis*, *Salmonella pullorum/gallinarum* and *Salmonella dublin* genomes as templates had target bands (FIG. 2 and FIG. 3). Sequencing results after gel recovery showed that the nucleotide similarity of all tcpS genes was 100%. It shows that by means of the specific tcpS amplification primers in the kit according to Embodiment 2, whether the unknown bacteria are *Salmonella* of these three serotypes can be rapidly identified with the PCR method.

Embodiment 4 Application of Kit in Pig Farm

By using the kit according to Embodiment 2 to detect 128 *Salmonella* strains, the three serotypes, i.e., *Salmonella enteritidis*, *Salmonella pullorum/gallinarum* and *Salmonella dublin* can be detected rapidly and accurately. The detection steps are as follows:

(1) Isolating *Salmonella*

In this experiment, samples were collected from a pig farm in Jiangsu Province, China, and the collection of the samples, enrichment of bacteria, isolation and physiological and biochemical identification of *Salmonella* refer to the methods established in the prior art (Li Y, et al. Food Control, 2016; Cai Y, et al. Int J Food Microbiol, 2016). 128 *Salmonella* strains were totally isolated and identified in this experiment.

Figure 4A:
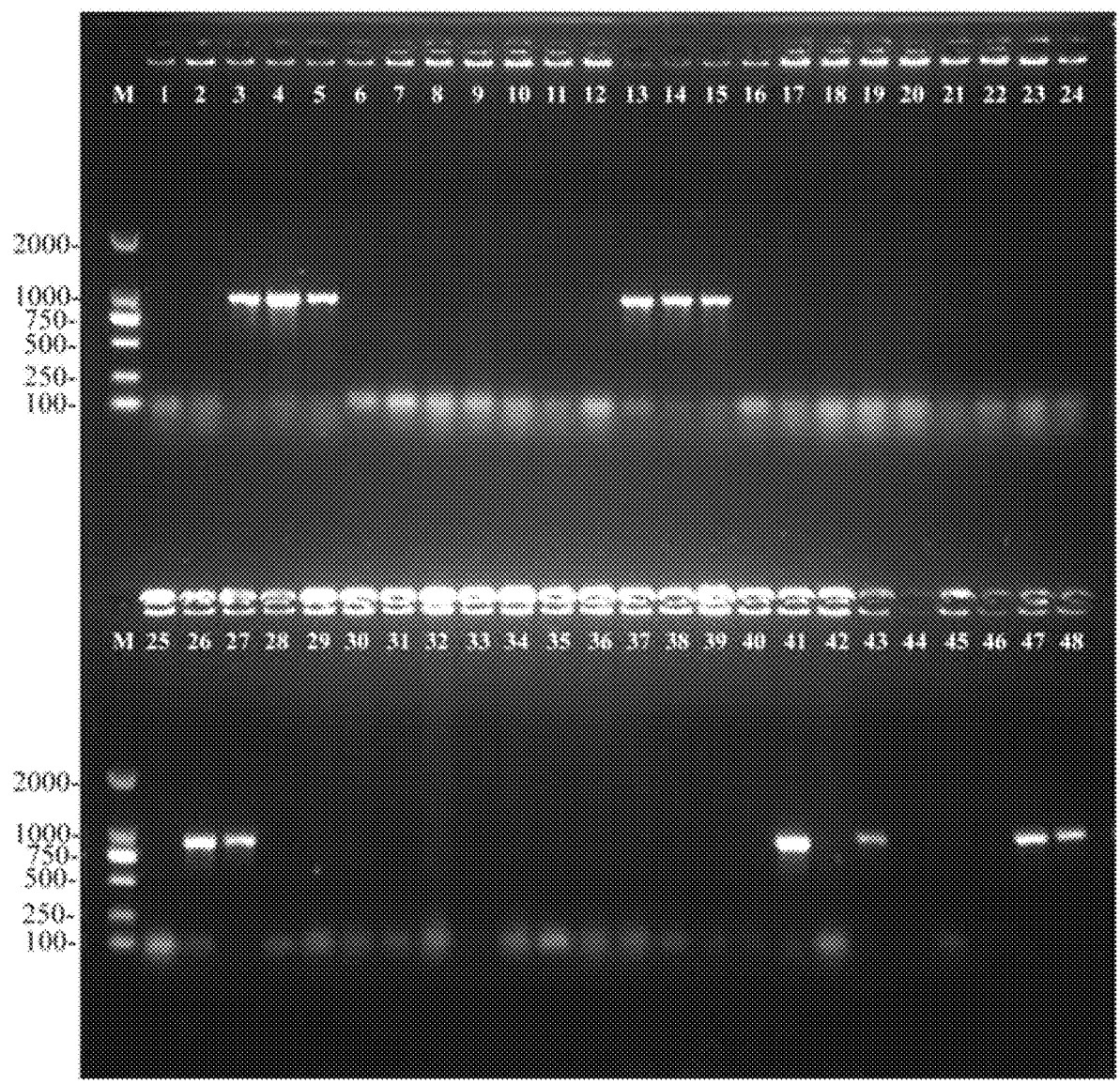
FIG. 4A is tcpS-containing bacteria in 1st-48th *Salmonella* strains identified by PCR, wherein the lane M is DL2000 Marker; lanes 1-48 are *Salmonella* isolated from pig farms, and the lane where the target band can be amplified is one of the three serotypes: *Salmonella enteritidis, Salmonella pullorum/gallinarum* or *Salmonella dublin*.
Figure 4B:
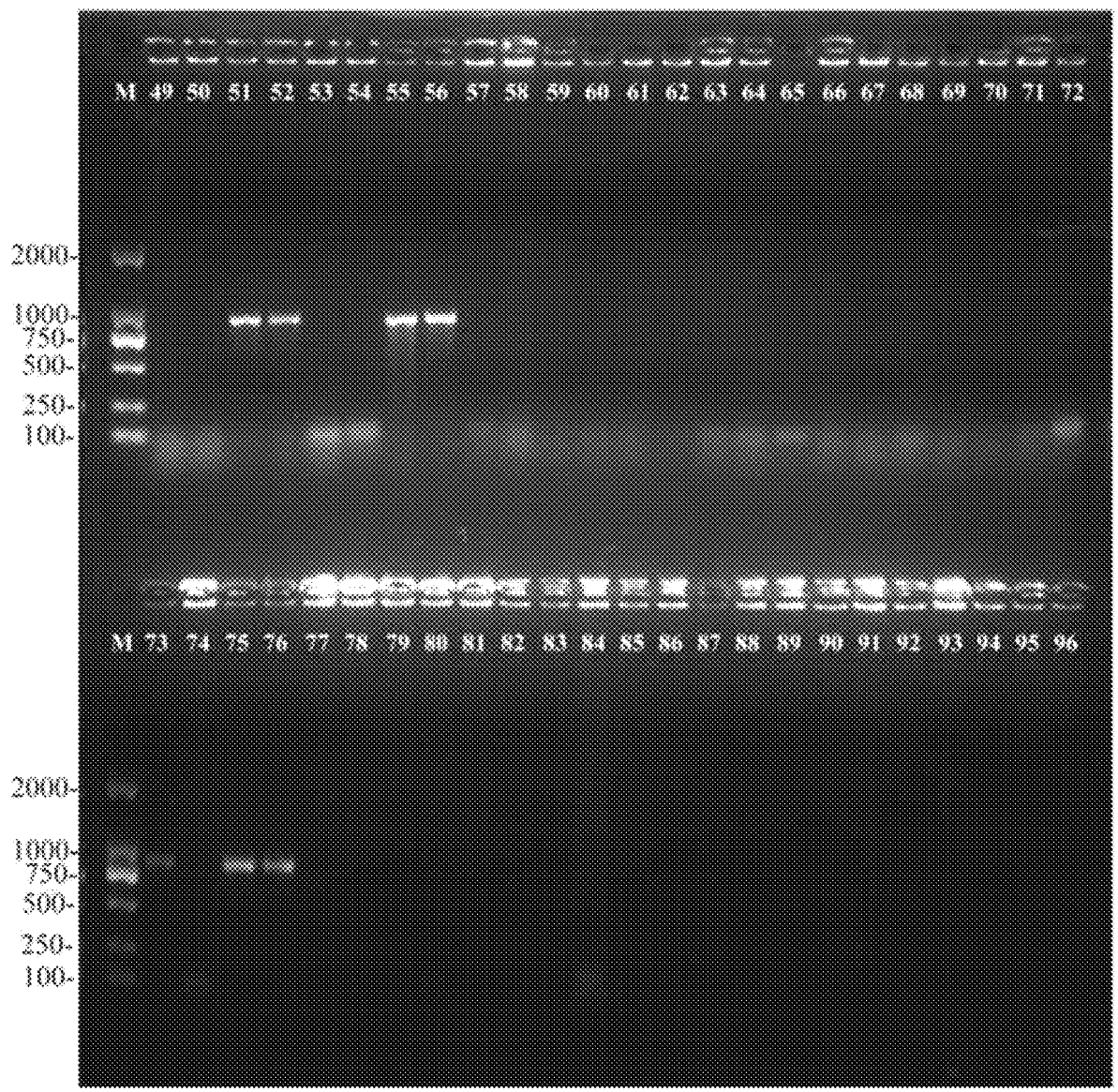
FIG. 4B is tcpS-containing bacteria in 49th-96th *Salmonella* strains identified by PCR, wherein the lane M is DL2000 Marker; lanes 49-96 are *Salmonella* isolated from pig farms, and the lane where the target band can be amplified is one of the three serotypes: *Salmonella enteritidis, Salmonella pullorum/gallinarum* or *Salmonella dublin*.
Figure 4C:
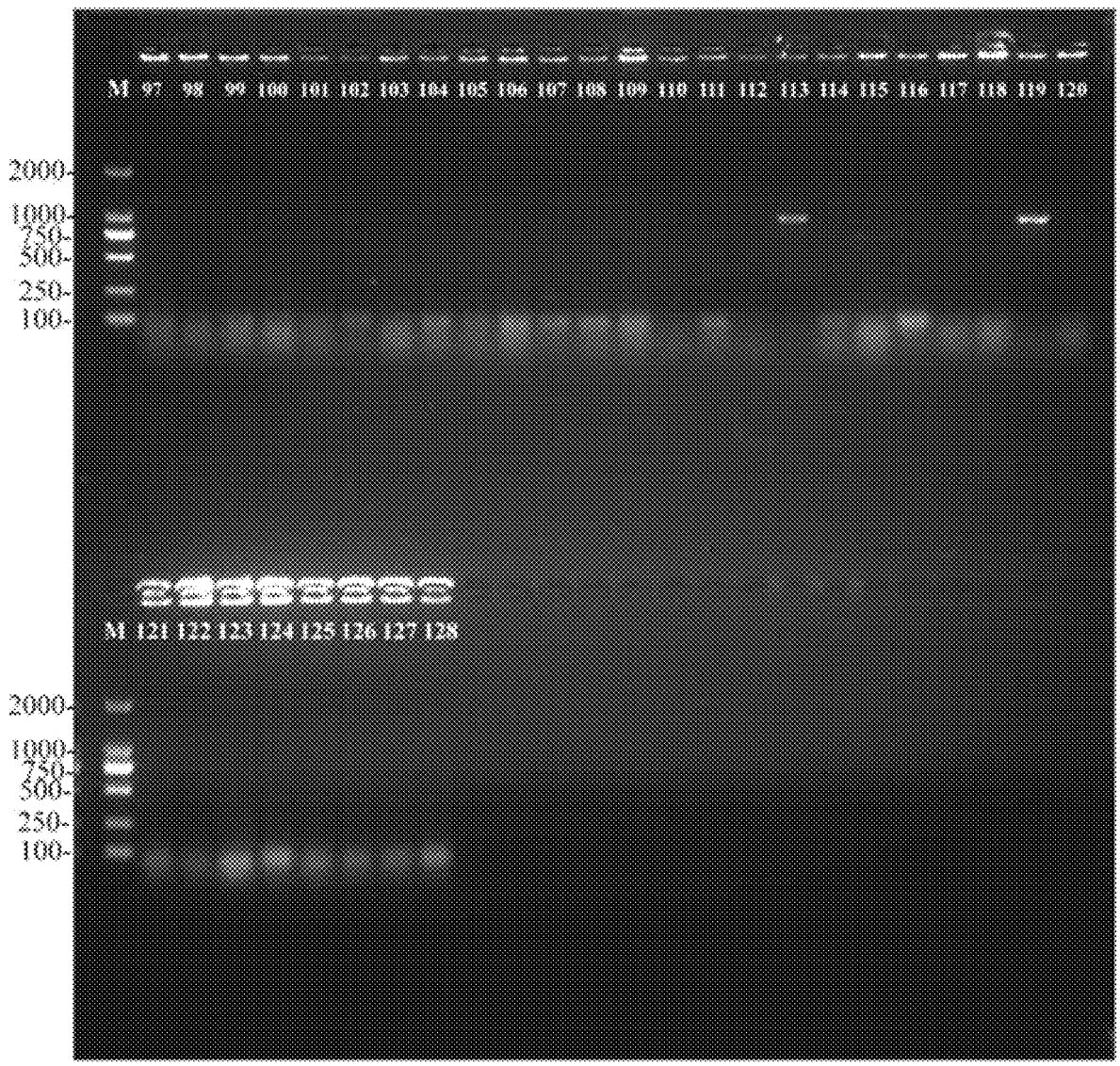
FIG. 4C is tcpS-containing bacteria in 97th-128th *Salmonella* strains identified by PCR, wherein the lane M is DL2000 Marker; lanes 97-128 are *Salmonella* isolated from pig farms, and the lane where the target band can be amplified is one of the three serotypes: *Salmonella enteritidis, Salmonella pullorum/gallinarum* or *Salmonella dublin*.

(2) Detecting *Salmonella enteritidis*, *Salmonella pullorum/gallinarum* and *Salmonella dublin* in the Samples By Using PCR Method 128 *Salmonella* strains were inoculated into an LB liquid culture medium and cultured overnight at 37° C. and 180 rpm, and the tcpS gene was amplified using a bacteria solution as a template the next day. The PCR reaction system was (25 μL): ddH$_2$O 16.25 μL, dNTP 2 μL, 10× PCR buffer 2.5 μL, tcpS-F 1 μL, tcpS-R 1 μL, template (bacteria solution) 2 μL, rTaq enzyme 0.25 μL. The PCR procedure was maintaining at 94° C. for 5 min; maintaining at 94° C. for 45 s, at 59° C. for 45 s, at 72° C. for 1 min as a cycle, performing this cycle for 30 times; then maintaining at 72° C. for 10 min. PCR products were subjected to 1% agarose gel electrophoresis, and the bacterium which could amplify tcpS target bands was one of the three serotypes: *Salmonella enteritidis*, *Salmonella pullorum/gallinarum* or *Salmonella dublin*. The results showed that 21 the of 128 *Salmonella* strains contained tcpS gene, which were No. 3, 4, 5, 13, 14, 15, 26, 27, 41, 43, 47, 48, 51, 52, 55, 56, 73, 75, 76, 113 and 119 (FIG. 4). These *Salmonella* strains each was one of the three serotypes: *Salmonella enteritidis*, *Salmonella pullorum/gallinarum* or *Salmonella dublin*.

(3) Traditional Serotype Identification of *Salmonella*

The serotype identification of the 128 *Salmonella* strains isolated in this experiment refers to the method established in the prior art (Li Y, et al. Food Control, 2016; Cai Y, et al. Int J Food Microbiol, 2016). Serotype identification results showed that there were 21 *Salmonella enteritidis* strains out of the 128 *Salmonella* strains, which were No. 3, 4, 5, 13, 14, 15, 26, 27, 41, 43, 47, 48, 51, 52, 55, 56, 73, 75, 76, 113 and 119. The PCR detection results were completely consistent with serotype identification results.

In this embodiment, it took at least 2 days to screen *Salmonella* which is one of the three serotypes: *Salmonella enteritidis*, *Salmonella pullorum/gallinarum* and *Salmonella dublin* out of the 128 *Salmonella* strains by a serotype identification method. However, by using the detection kit according to Embodiment 2 of the present disclosure, it only took 3 hours to screen *Salmonella* which is one of the three serotypes: *Salmonella enteritidis*, *Salmonella pullorum/gallinarum* and *Salmonella dublin* out of the 128 *Salmonella* strains, and the accuracy rate is 100%.

Embodiment 5 Application of Kit in Chicken Farm

By using the kit according to Embodiment 2 to detect 22 *Salmonella* strains, the three serotypes, i.e., *Salmonella enteritidis*, *Salmonella pullorum/gallinarum* and *Salmonella dublin* can be detected rapidly and accurately. The detection steps are as follows:

(1) Isolating *Salmonella*

In this experiment, samples were collected from a chicken farm in Jiangsu province, China, and the collection of the samples, enrichment of bacteria, isolation and physiological and biochemical identification of *Salmonella* refer to the methods established in the prior art (Li Y, et al. Food Control, 2016; Cai Y, et al. Int J Food Microbiol, 2016). 22 *Salmonella* strains were isolated and identified in this experiment.

Figure 5:
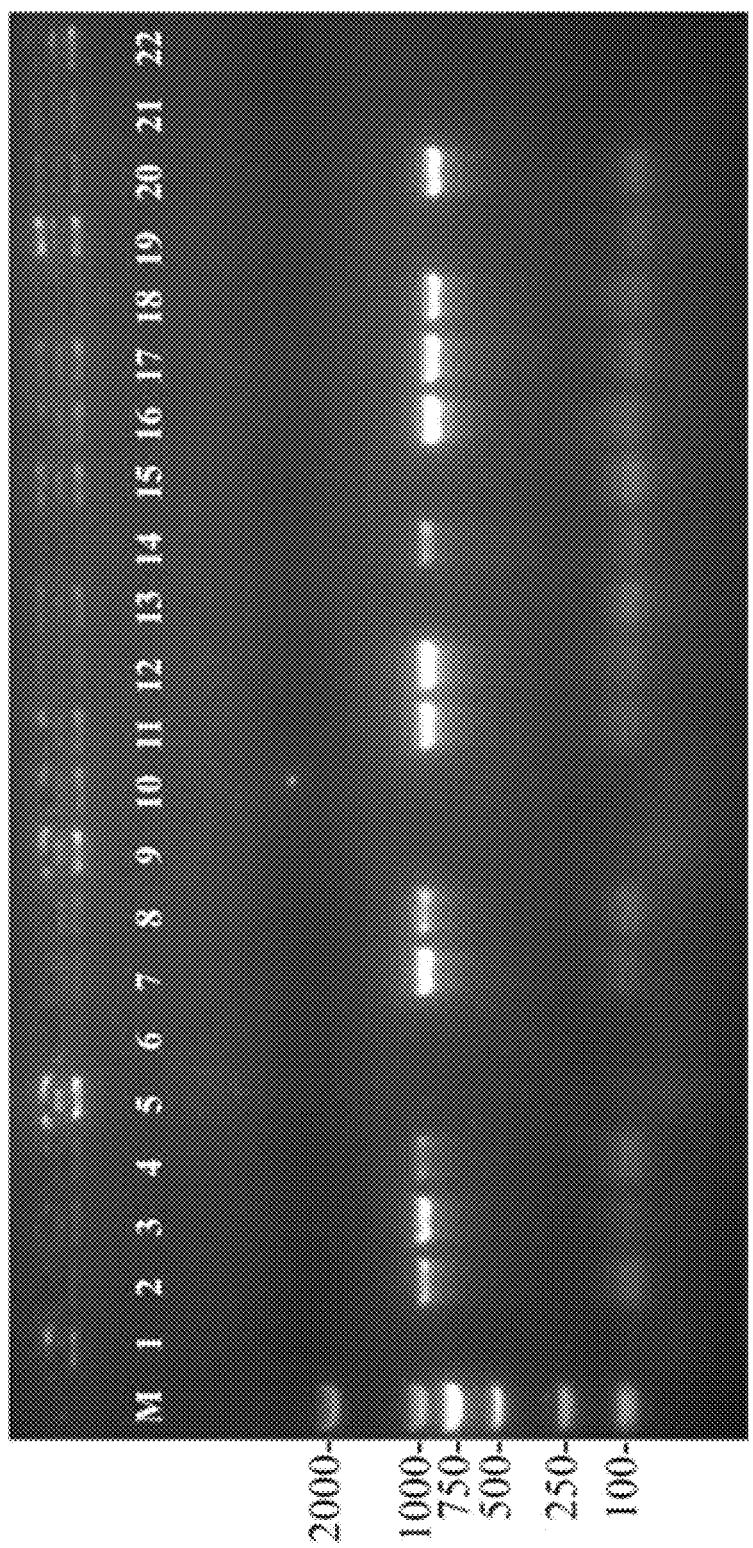
FIG. 5 is tcpS-containing bacteria in 1st-22nd *Salmonella* strains identified by PCR, wherein the lane M is DL2000 Marker; lanes 1-22 are *Salmonella* isolated from chicken farms, and the lane where the target band can be amplified is one of the three serotypes: *Salmonella enteritidis, Salmonella pullorum/gallinarum* or *Salmonella dublin*.

(2) Detecting *Salmonella enteritidis*, *Salmonella pullorum/gallinarum* and *Salmonella dublin* in the Samples By Using PCR Method 22 *Salmonella* strains were inoculated into an LB liquid culture medium and cultured overnight at 37° C. and 180 rpm, and the tcpS gene was amplified using a bacteria solution as a template the next day. The PCR reaction system was (25 μL): ddH$_2$O 16.25 μL, dNTP 2 μL, 10× PCR buffer 2.5 μL, tcpS-F 1 μL, tcpS-R 1 μL, template (bacteria solution) 2 μL, rTaq enzyme 0.25 μL. The PCR procedure was maintaining at 94° C. for 5 min; maintaining at 94° C. for 45 s, at 59° C. for 45 s, at 72° C. for 1 min as a cycle, performing this cycle for 30 times; then maintaining at 72° C. for 10 min. PCR products were subjected to 1% agarose gel electrophoresis, and the bacterium which could amplify tcpS target bands was one of the three serotypes: *Salmonella enteritidis*, *Salmonella pullorum/gallinarum* or *Salmonella dublin*. Results showed that 12 of the 22 *Salmonella* strains contained the tcpS gene, which were No. 2, 3, 4, 7, 8, 11, 12, 14, 16, 17, 18 and 20 (FIG. 5). These *Salmonella* strains each was one of the three serotypes: *Salmonella enteritidis*, *Salmonella pullorum/gallinarum* or *Salmonella dublin*.

3) Traditional Serotype Identification of *Salmonella*

The serotype identification of 22 *Salmonella* strains isolated in this experiment refers to the methods established in the prior art (Li Y, et al. Food Control, 2016; Cai Y, et al. Int J Food Microbiol, 2016). Serotype identification results showed that 12 *Salmonella* out of the 22 *Salmonella* strains are *Salmonella* pullorum strains, which were no. 2, 3, 4, 7, 8, 11, 12, 14, 16, 17, 18 and 20. The PCR detection results were completely consistent with serotype identification results.

In this embodiment, it took at least 2 days to screen *Salmonella* which is one of the three serotypes: *Salmonella enteritidis*, *Salmonella pullorum/gallinarum* or *Salmonella dublin* out of the 22 *Salmonella* strains by the serotype identification method. However, by using the detection kit according to Embodiment 2 of the present disclosure, it only took 3 hours to accurately screen *Salmonella* which is one of the three serotypes: *Salmonella enteritidis*, *Salmonella pul-* lorum/gallinarum or *Salmonella dublin* out of the 22 *Salmonella* strains, and the accuracy rate is 100%.

Embodiment 6 Application of Kit in Cattle Farm

By using the kit according to Embodiment 2 to detect 11 *Salmonella* strains, the three serotypes, i.e., *Salmonella enteritidis*, *Salmonella pullorum/gallinarum* and *Salmonella dublin* can be detected rapidly and accurately. The detection steps are as follows:

(1) isolating *Salmonella*

In this experiment, samples were collected from a cattle farm in Jiangsu Province, China, and the collection of samples, enrichment of bacteria, isolation and physiological and biochemical identification of *Salmonella* refer to the established methods in the prior art (Li Y, et al. Food Control, 2016; Cai Y, et al. Int J Food Microbiol, 2016). 11 *Salmonella* strains were isolated and identified in this experiment.

Figure 6:
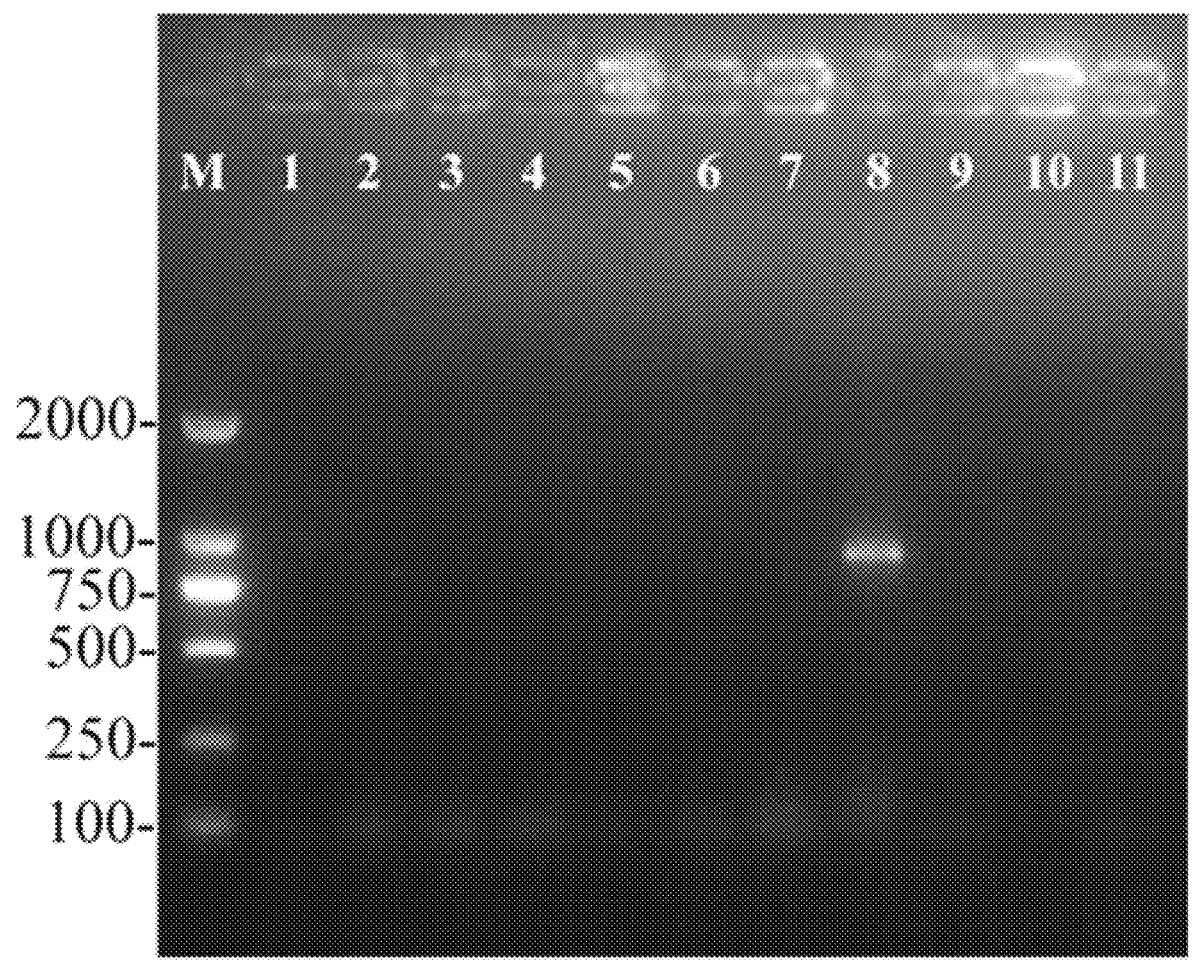
FIG. 6 is tcpS-containing bacteria in 1st-11th *Salmonella* strains identified by PCR, wherein the lane M is DL2000 Marker; lanes 1-11 are *Salmonella* isolated from cattle farms, and the lane where the target band can be amplified is one of the three serotypes: *Salmonella enteritidis, Salmonella pullorum/gallinarum* or *Salmonella dublin*.

(2) Detecting *Salmonella enteritidis*, *Salmonella pullorum/gallinarum* and *Salmonella dublin* in the Samples By Using PCR Method 11 *Salmonella* strains were inoculated into an LB liquid culture medium and cultured overnight at 37° C. and 180 rpm, and the tcpS gene was amplified using a bacteria solution as a template the next day. The PCR reaction system was (25 μL): ddH$_2$O 16.25 μL, dNTP 2 μL, 10× PCR buffer 2.5 μL, tcpS-F 1 μL, tcpS-R 1 μL, template (bacteria solution) 2 μL, rTaq enzyme 0.25 μL. The PCR procedure was maintaining at 94° C. 5 min; maintaining at 94° C. for 45 s, at 59° C. for 45 s, at 72° C. for 1 min as a cycle, performing this cycle for 30 times; then maintaining at 72° C. for 10 min. PCR products were subjected to 1% agarose gel electrophoresis, and the bacterium which could amplify tcpS target bands was one of the three serotypes: *Salmonella enteritidis*, *Salmonella pullorum/gallinarum* or *Salmonella dublin*. Results showed that only No. 8 sample of the 11 *Salmonella* strains contained the tcpS gene (FIG. 6), and the *Salmonella* was one of the three serotypes: *Salmonella enteritidis*, *Salmonella pullorum/gallinarum* or *Salmonella dublin*.

3) Traditional Serotype Identification of *Salmonella*

The serotype identification of 11 *Salmonella* strains isolated in this experiment refers to the methods established in the prior art (Li Y, et al. Food Control, 2016; Cai Y, et al. Int J Food Microbiol, 2016). Serotype identification results showed that there was 1 *Salmonella dublin* strain out of the 11 *Salmonella* strains, which was No. 8 isolate. The PCR detection results were completely consistent with serotype identification results.

In this embodiment, it took at least 2 days to screen *Salmonella* which is one of the three serotypes: *Salmonella enteritidis*, *Salmonella pullorum/gallinarum* or *Salmonella dublin* out of the 11 *Salmonella* strains by the serotype identification method. However, by using the detection kit according to Embodiment 2 of the present disclosure, it only took 3 hours to accurately screen *Salmonella* which is one *Salmonella* of the three serotypes: *Salmonella enteritidis*, *Salmonella pullorum/gallinarum* or *Salmonella dublin* out of the 11 *Salmonella* strains, and the accuracy rate is 100%.

To sum up, the kit according to the present disclosure has the following advantages:

In traditional serotype identification, a specific *Salmonella* serotype identification kit is required, which is expensive and cumbersome, especially during isolation of *Salmonella* of a specific serotype (e.g. *Salmonella enteritidis*, *Salmonella pullorum/gallinarum* or *Salmonella dublin*) from a large sample, it takes a large amount of time (at least 2 days) and involves a large amount of work, and the result is judged by the naked eyes, so there may be human errors. While, the detection method of the kit according to the present disclosure is simple to operate and very low in cost, and has no requirement on the existence form of bacteria (single colony, frozen bacteria solution or fresh bacteria solution can be used), the whole identification process can be completed within 3 hours (comprising PCR and agarose gel electrophoresis), and the accuracy rate reaches 100%.

Therefore, the PCR detection kit for rapidly identifying *Salmonella* of specific serotypes according to the present disclosure helps to simplify the traditional steps for identifying *Salmonella* serotypes, and provides a new method for rapidly identifying *Salmonella* of *enteritidis*, *pullorum* disease/*gallinarum*, and Dublin serotypes in a large number of samples.

The above-described embodiments merely illustrate the principles and effects of the present disclosure, but are not intended to limit the present disclosure. Any person skilled in the art can modify or change the above embodiments without departing from the spirit and scope of the present disclosure. Therefore, all equivalent modifications or changes made by persons of ordinary skill in the art without departing from the spirit and technical thought disclosed in the present disclosure shall still be covered by the claims of the present disclosure.

What is claimed is:

1. A method for detecting *Salmonella enteritidis, Salmonella pullorum/gallinarum* or *Salmonella dublin*, comprising:
   (1) extracting sample genomic DNA;
   (2) adding the sample genomic DNA, a positive control or a negative control into PCR tubes of a PCR reaction system respectively to obtain a corresponding sample reaction tube, positive reaction tube or negative reaction tube, wherein the PCR reaction system contains the primers comprising a forward primer having a nucleotide sequence as set forth in SEQ ID NO:1 and a reverse primer having a nucleotide sequence as set forth in SEQ ID NO:2 for detecting the tcpS gene;
   (3) placing the reaction tubes on a PCR instrument, setting circulation parameters, and performing a PCR reaction; and
   (4) analyzing results after the PCR reaction is completed by performing an agarose gel electrophoresis, wherein when the sample consists of at least one of *Salmonella enteritidis, Salmonella pullorum/gallinarum*, and *Salmonella dublin*, a band at 882 bp amplified by the tcpS gene forward and reverse primers is detected in the agarose gel electrophoresis;
   wherein when the sample consists of none of *Salmonella enteritidis, Salmonella pullorum/gallinarum*, and *Salmonella dublin*, a band at 882 bp amplified by the tcpS gene forward and reverse primers is not detected in the agarose gel electrophoresis.

2. The method according to claim 1, wherein the method is not used for disease diagnosis purpose.

3. The method according to claim 1, wherein in step (3), PCR reaction conditions are set to be: (a) maintaining at 94° C. for 5 min; (b) maintaining at 94° C. for 45 s; (c) maintaining at 59° C. for 45 s; (d) maintaining at 72° C. for 1 min, performing (b) to (d) for 30 times, and then (e) maintaining at 72° C. for 10 min.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Artificial
<220> FEATURE:
<223> OTHER INFORMATION: tcpS-F

<400> SEQUENCE: 1
atgtctataa gcaccacaat g                    21

<210> SEQ ID NO 2
<211> LENGTH: 22
<212> TYPE: DNA
<213> ORGANISM: Artificial

```
<220> FEATURE:
<223> OTHER INFORMATION: tcpS-R

<400> SEQUENCE: 2
tcatttcaat aatgattcaa gc                                               22
```